United States Patent [19]

Kamuro et al.

[11] Patent Number: 4,846,872
[45] Date of Patent: Jul. 11, 1989

[54] HERBICIDE

[75] Inventors: Yasuo Kamuro; Tadahide Kawai; Toshihito Kakiuchi, all of Ibaraki, Japan

[73] Assignee: Fujisawa Pharmaceutical Co., Ltd., Japan

[21] Appl. No.: 82,043

[22] Filed: Aug. 5, 1987

[30] Foreign Application Priority Data

Aug. 11, 1986 [JP] Japan ................................ 61-188085

[51] Int. Cl.[4] ........................................... A01N 57/00
[52] U.S. Cl. ......................................... 71/86; 71/120; 71/93
[58] Field of Search ................................ 71/120, 86

[56] References Cited

U.S. PATENT DOCUMENTS

| 2,709,648 | 5/1955 | Ryker et al. | 71/120 |
| 4,206,156 | 6/1980 | Kamiya et al. | 558/173 |
| 4,613,354 | 9/1986 | Rusch | 71/120 |
| 4,692,181 | 9/1987 | Buringer et al. | 71/120 |

OTHER PUBLICATIONS

Yamaji et al., "N-substituted alkyl amine phosphates as herbicides" CA 105: 166897j (1986).
C. R. Worthing et al.: "Pesticide Manual", 7th Edition, pp. 226, 250, 1983, British Crop Protection Council, Groydon, GB, p. 11, Entry 250; p. 226, Entry 5400.

Primary Examiner—Richard L. Raymond
Assistant Examiner—Amelia A. Owens
Attorney, Agent, or Firm—Jordan B. Bierman; Bierman and Muserlian

[57] ABSTRACT

This invention relates to a herbicidal composition comprising fosmidomycin or salt thereof in combination with the other herbicide selected from the group of ametryn or salt thereof or diuron, and to a method of killing weeds by applying to weed seedlings the said combination.

5 Claims, No Drawings

HERBICIDE

This invention relates to a new herbicide.

More particularly, it relates to a new herbicidal composition comprising fosmidomycin or salt thereof in combination with the other herbicide selected from the group or ametryn or salt thereof or diuron, and to a method of killing weeds by applying to weed seedlings the said combination.

The fosmidomycin is a known compound, 3-(N-formyl-N-hydroxyamino)propylphosphonic acid as antibacterial agent [Cf. European Journal of Drug Metabolism and Pharmacokinetics Vol. 7, P59 (1982)] and as herbicide [Cf. Japan Kokai No. 106504/1986].

Further, ametryn and diuron are also known herbicides, 2-methylmercapto-4-ethylamino-6-isopropylamino-s-triazine and 3-(3,4-Dichlorophenyl)-1,1-dimethylurea, respectively [Cf. The Merck Index tenth edition items 392 and 3400 (1983)].

The fundamental physiological action of fosmidomycin resides in the inhibition of production of chlorophyll. Therefore, plants emerging after treatment with fosmidomycin are ready to undergo chlorosis. When the treating concentration is such that this chlorosis lasts as long as more than 2 to 3 weeks, arrest of growth occurs as the plant is prevented from nursing itself by photosyntheses, leading to decay. However, as the treating concentration is decreased, the degree and duration of chlorosis are lessened and the plant will not die but show a recovery of growth so that the object of killing cannot be accomplished. While a large variety of herbicides have been developed and put to use for controlling the weeds detrimental to crop plants and the environment, each of these herbicides has its own drawback or shortcoming and none has ever proved fully satisfactory in weed killing effect.

Thus, what are mainly desired in herbicides are:
(1) The maximum possible coverage of weed varieties that can be controlled (a broad herbicidal spectrum)
(2) Manifestation of sufficient control effect within the shortest possible time after application (a reduced number of days required for complete weed control)
(3) No variation in effect according to the volume and height of weeds or an improved stability of control effect (stabilized weed control effect).
(4) Reduced amounts of active substances required for control (reduced herbicide consumption)

The present inventors discovered that application of a composition containing fosmidomycin or salt thereof in combination with the other herbicide selected from the group of ametryn or salt thereof and diuron to a plant resulted in a surprisingly great synergistic herbicidal effect on the plant. This finding was followed by a further investigation, which culminated in the present invention.

The salt of fosmidomycin may include an agronomically acceptable salt thereof such as a base salt (e.g. sodium salt, potassium salt, calcium salt, etc.) and the like.

The salt of ametryn may include an agronomically acceptable salt thereof such as an acid addition (e.g. hydrochloride, sulfate, phosphate, etc.) and the like.

The herbicidal composition according to the present invention displays remarkable efficacy as a postemergence herbicide, and is preferably applied to the whole stalks and foliage of weeds that have emerged.

Moreover, the herbicidal composition of the present invention provides effective control, irrespective of weed variety, e.g. broad-leaved weeds and grasses.

The application rate for the active ingredients in the herbicidal composition of the invention varies according to the combination used and kinds of weeds to be controlled. Generally however, the optimum rate of application is selected from the range of 5 to 1000 grams/10 ares and preferably from the range of 100 to 500 grams/10 ares.

The ratio of the fosmidomycin or a salt thereof to the ametryn or a salt thereof or diuron in the herbicidal composition of the invention is dependent on the kinds of respective compounds and the kinds of weeds to be controlled.

Generally, the ratio is selected from the range of 10:1 to 1:10, preferably 6:1 to 1:6.

To apply the herbicidal composition of the invention, it can be mixed with a carrier suited to the intended usage and applied in such varied forms as dusts, granular preparations, wettable powders, liquid preparations, emulsifiable concentrates, flowable emulsion concentrates and so on. The carrier mentioned just above may be a solid or a liquid carrier or a combination thereof. As examples of said carrier, there may be mentioned finely divided minerals such as kaolinite, bentonite, pyrophyllite, talc, diatomaceous earth, silica gel, calcium carbonate, etc., finely divided vegetable materials such as starch, gum arabic, etc., organic solvents such as alcohols, ketones, kerosine, benzene, toluene, xylene, cyclohexane, methylnaphthalene, dioxane, dimethylformamide, dimethyl sulfoxide, corn oil, o-dichlorobenzene, isophorone, water and so on. Further, agronomically acceptable adjuvants and auxiliaries such as wetting agents, dispersing agents, adhesives, extenders, etc. can be incorporated, if necessary, in appropriate proportions.

Each of these preparations is not only useful as such but may be used in combination with bactericides, fungicides, nematocides, insecticides, plant growth regulators, fertilizers, other herbicides and so on.

The following reference and working examples are intended to illustrate the invention in further detail.

REFERENCE EXAMPLE

Seeds of the following species of plants were sown in soil-filled pots (30 cm long × 10 cm wide × 10 cm deep) and grown in a glasshouse. After 2 weeks, seedlings which had grown to a height of 5 to 20 cm were treated with test compound. The test compound was dissolved in water and the solution was adjusted to a application concentration of 500 ppm or 5000 ppm and applied to the whole surface of the plant at the rate of 100 liters water/10 ares. Control pots were treated with water only. After 10, 20 and 30 days following application, the plants were observed for growth and the control effect of the test compound was evaluated.

The test plants were as follows.

| No. | Test plant Common name | Botanical name |
|---|---|---|
| 1 | Rice | Oryza sativa L. |
| 2 | Maize | Zea mays L. |
| 3 | Barnyard millet | Panicum Crus-galli L. |
| 4 | Crabgrass | Digitaria adscendes Henr. |
| 5 | Soybean | Glycine Max MERR. |
| 6 | Convolvulus | Calystegia japonica choisy |
| 7 | Barnyard grass | Amaranthus Blitum L |

The test compound is as follows.

| Compound No. | Chemical name |
|---|---|
| 1 | 3-(N—Formyl-N—hydroxyamino)propyl-phosphonic acid monosodium salt |

The test results are set forth below in the table. Control effects were scored on a rating scale of 0 for no effect through 100 for complete control (complete kill).

| Compound No. (concentration) | Time after application in days | Plant No. Herbicidal activity (%) | | | | | | |
|---|---|---|---|---|---|---|---|---|
| | | 1 | 2 | 3 | 4 | 5 | 6 | 7 |
| 1 (500 ppm) | 10 | ○22 | ○27 | ○34 | ○40 | ○46 | ○25 | ○28 |
| | 20 | ○56 | ○44 | ○61 | ○67 | ○60 | ○40 | ○43 |
| | 30 | 38 | 31 | 55 | 52 | 42 | 10 | 27 |
| 1 (5000 ppm) | 10 | ○51 | ○65 | ○72 | ○78 | ○59 | ○52 | ○69 |
| | 20 | 100 | 100 | 100 | 100 | 100 | 100 | 100 |
| | 30 | 100 | 100 | 100 | 100 | 100 | 100 | 100 |

The open circle around each figure indicates the occurrence of chlorosis.

EXAMPLE 1

Using the same test plant species and the same test procedure as described in Reference Example, the control effects of the following compounds were tested and evaluated.

The observation of plants for growth status was made on 10 days after application.

The test compounds are as follows.

| Compound No. | Chemical name (concentration) |
|---|---|
| 1 | 2-Methylmercapto-4-ethylamino-6-isopropylamino-s-triazine 1* (500 ppm) |
| 2 | 2-Methylmercapto-4-ethylamino-6-isopropylamino-s-triazine 1* (500 ppm) + 3-(N—Formyl-N—hydroxyamino)propylphosphonic acid monosodium salt (500 ppm) |
| 3 | 3-(N—Formyl-N—hydroxyamino)propylphosphonic acid monosodium salt (500 ppm) |

Note
As test compounds 1*, the corresponding commercial product Gesapax (25% emulsifiable concentrate, Ciba-Geigy) was used.

The test results are shown below in the table.

| Compound No. | Plant No. Hibicidal activity (%) | | | | | | |
|---|---|---|---|---|---|---|---|
| | 1 | 2 | 3 | 4 | 5 | 6 | 7 |
| 1 (Control) | 78 | 82 | 100 | 100 | 100 | 80 | 78 |
| 2 | 100 | 100 | 100 | 100 | 100 | 100 | 100 |
| 3 (Control) | ○22 | ○27 | ○34 | ○40 | ○46 | ○25 | ○28 |

The open circle around each figure indicates the occurrence of chlorosis.

EXAMPLE 2

The field on which the following weeds were grown, were plotted out in a ratio of 4 m²/lot.

The following test compound was dissolved in water at the specified application rate and was sprayed onto the whole surface of the weeds at the volume rate of 100 liters water/10 ares.

Control lots were treated with water only.

| Test weed code | Test weeds common name | Botanical name | height (cm) |
|---|---|---|---|
| a | Fleabane, Annul | Erigeron annuus L. | 60 |
| b | Ohinutade | Polygonum Blumei Meisn | 60 |
| c | Clover, Red | Trifolium protense L. | 40 |
| d | Mugwort | Artemisia vulgaris L. var. indica Maxim | 40 |
| e | Dandelion | Taraxacum Officinale Weber | 10–20 |
| f | Brome, Rescue | Bromus unioloides Humb. Bonpl. et Kunth | 60 |

| Test compound No. | Chemical name |
|---|---|
| A | 3-(N—Formyl-N—hydroxyamino)-propylphosphonic acid monosodium salt |
| B | 2-Methylmercapto-4-ethylamino-6-isopropylamino-s-triazine 1** |
| C | 3-(3,4-Dichlorophenyl)-1,1-dimethylurea 2** |

Note
As test compounds 1 and 2, the corresponding commercial products, Gesapax (25% emulsifiable concentrate, Ciba-Geigy) and Karmex D(78.5% wettable powder, du Pont) were used, respectively.

Two weeks after the treatment, herbicidal effect of the test compounds on the weeds were observed and scored on a rating scale of 0 for no effect through—100 for complete kill.

| Test compound and application rate (g/10a) | | Test weed and herbicidal activity (%) | | | | | |
|---|---|---|---|---|---|---|---|
| B | A | a | b | c | d | e | f |
| 0 | 25 | 5 | 5 | 5 | 10 | 10 | 0 |
| 0 | 50 | 10 | 10 | 10 | 15 | 10 | 10 |
| 0 | 100 | 20 | 20 | 20 | 30 | 15 | 10 |
| 62.5 | 0 | 0 | 0 | 0 | 0 | 0 | 0 |
| 125 | 0 | 20 | 20 | 15 | 20 | 10 | 15 |
| 250 | 0 | 40 | 50 | 60 | 60 | 60 | 55 |
| 62.5 | 25 | 60 | 60 | 50 | 60 | 70 | 60 |
| 125 | 25 | 70 | 65 | 70 | 80 | 70 | 70 |
| 250 | 25 | 85 | 80 | 85 | 80 | 85 | 80 |
| 62.5 | 50 | 70 | 70 | 75 | 80 | 70 | 70 |
| 125 | 50 | 80 | 80 | 90 | 90 | 80 | 80 |
| 250 | 50 | 90 | >90 | 90 | >90 | 90 | 90 |

-continued

| Test compound and application rate (g/10a) | Test weed and herbicidal activity (%) | | | | | |
| --- | --- | --- | --- | --- | --- | --- |
| 62.5 | 100 | 80 | 90 | 80 | >90 | 80 | 80 |
| 125 | 100 | 90 | >90 | >90 | >90 | 90 | 90 |
| 250 | 100 | >90 | >90 | >90 | >90 | >90 | >90 |

| C | A | a | b | c | d | e | f |
| --- | --- | --- | --- | --- | --- | --- | --- |
| 0 | 25 | 5 | 5 | 5 | 10 | 10 | 0 |
| 0 | 50 | 10 | 10 | 10 | 25 | 10 | 10 |
| 0 | 100 | 20 | 20 | 20 | 30 | 15 | 10 |
| 250 | 0 | 5 | 5 | 10 | 5 | 10 | 5 |
| 500 | 0 | 15 | 10 | 20 | 15 | 20 | 15 |
| 750 | 0 | 40 | 30 | 40 | 30 | 40 | 30 |
| 250 | 25 | 40 | 50 | 30 | 50 | 50 | 40 |
| 500 | 25 | 60 | 60 | 40 | 50 | 55 | 60 |
| 750 | 25 | 85 | 80 | 75 | 85 | 85 | 85 |
| 250 | 50 | 60 | 70 | 50 | 70 | 60 | 60 |
| 500 | 50 | 80 | 90 | 80 | 90 | 90 | 85 |
| 750 | 50 | 90 | 90 | 90 | >90 | 90 | 90 |
| 250 | 100 | 85 | 90 | 80 | 90 | 80 | 70 |
| 500 | 100 | 90 | >90 | >90 | >90 | >90 | >90 |
| 750 | 100 | >90 | >90 | >90 | >90 | >90 | >90 |

EXAMPLE 3

Seeds of goosefoot were sown in soiled polyethylene pots (20 cm long × 10 cm wide × 10 cm deep) and grown in a glasshouse. Numbers of seedlings (Grown height: 30 cm) were adjusted to 10/pot. Each test compound was dissolved in water at the specified application rate and applied onto the leaves and stocks of Goosefoot. The treated goosefoot were grown in a glass house at 25°–30° C. for 2 weeks. The weight of the remaining and living portion (above ground) of groose foot was determined and from the obtained data, ratio (%) of the weight of treatment group to that of non-treatment group was calculated. The results are shown in the following table (a).

(a) Ratio (%) of the remaining weight of the treated plant to that of the non-treated plant

|  |  | application rate (g/10a) of the test compound A | | | |
| --- | --- | --- | --- | --- | --- |
|  |  | 0 | 25 | 50 | 100 |
| application rate (g/10a) of the test compound B | 0 | 100 | 95 | 85 | 85 |
|  | 62.5 | 100 | 45 | 25 | 10 |
|  | 125 | 80 | 20 | 10 | <10 |
|  | 250 | 50 | 10 | 10 | <10 |

Note:
Test compound A: 3-(N—formyl-N—hydroxyamino)-propylphosphonic acid monosodium salt
Test compound B: 2-methylmercapto-4-ethylamino-6-isopropylamino-s-triazine [Gesapax (25% emulsifiable concentrate, Ciba-Geigy)]

The above data were analyzed according to Colby's equation (cf. weeds, Vol, 15, P. 20–22).

| Expected value (%) of the remaining weight of the plant treated with the combination | | |
| --- | --- | --- |
| Obserbed value (%) of the remaining weight of the plant treated with compound A only | × | Observed value (%) of the remaining weight of the plant treated with compound B only |

In case that the expected value (%) is larger than the observed value (%), the combination can be judged to have synergistic effect.

The Colby's expected values (%) obtained by calculating using the above data are shown in the following table (b).

(b) Colby's expected value

|  |  | application rate (g/10a) of the test compound A | | |
| --- | --- | --- | --- | --- |
|  |  | 25 | 50 | 100 |
| application rate (g/10a) of the test compound B | 62.5 | 95 | 85 | 85 |
|  | 125 | 76 | 68 | 68 |
|  | 250 | 47.5 | 42.5 | 42.5 |

As clear from the data listed in the above table (a) and (b), all combinations of the test compound A and B can be judged to have synergistic herbicidal activity.

EXAMPLE 4

The following data were obtained in a similar manner to those of Example 3, excepting the test compound C was used in place of the compound B.

(a) Ratio (%) of the remaining weight of the treated plant to that of the non-treated plant

|  |  | application rate (g/10a) of the test compound A | | | |
| --- | --- | --- | --- | --- | --- |
|  |  | 0 | 25 | 50 | 100 |
| application rate (g/10a) of the test compound C | 0 | 100 | 95 | 85 | 85 |
|  | 250 | 95 | 60 | 40 | 20 |
|  | 500 | 85 | 45 | 10 | <10 |
|  | 750 | 60 | 20 | 10 | <10 |

Note:
Test compound A is the same compound as defined in Example 3.
Test compound C: 3-(3,4-dichlorophenyl)-1,1-dimethylurea[Karmex D (78.5% wettable powder, du Pont)].

(b) Colby's expected value (%)

|  |  | application rate (g/10a) of the test compound A | | |
| --- | --- | --- | --- | --- |
|  |  | 25 | 50 | 100 |
| application rate (g/10a) of the test compound C | 250 | 90 | 81 | 81 |
|  | 500 | 81 | 72 | 72 |
|  | 750 | 57 | 51 | 51 |

As clear from the data listed in the above table (a) and (b), all combinations of the test compound A and C can be judged to have synergistic herbicidal activity.

We claim:

1. A herbicidal composition comprising a herbicidally effective amount of fosmidomycin or a salt thereof in combination with the herbicide diuron, in a ratio of between 10:1 and 1:10, and an agronomically acceptable carrier or carriers.

2. A method of killing broad leaved weeds and grasses, said method comprising applying to broad leaf weeds or grass seedlings a herbicidally effective amount of a combination of fosmidomycin or a salt thereof and the herbicide diuron.

3. The herbicidal composition of claim 1 wherein said ratio is between 6:1 and 1:6.

4. The method of claim 2 wherein said combination is applied in an amount of 5 to 1000 g/1000 $m^2$.

5. The method of claim 2 wherein said combination is applied in an amount of 100 to 500 g/1000 $m^2$.

* * * * *